United States Patent
Kim et al.

(10) Patent No.: US 9,175,412 B2
(45) Date of Patent: Nov. 3, 2015

(54) IRON-GOLD BARCODE NANOWIRE AND MANUFACTURING METHOD THEREOF

(75) Inventors: Young Keun Kim, Seoul (KR); Ju Hun Lee, Seoul (KR); Jun Hua Wu, Seoul (KR); Hong Ling Liu, Seoul (KR); Ji Ung Cho, Uiwang-si (KR); Ji Hyun Min, Seoul (KR); Boo Hyun An, Goyang-si (KR); Moon Kyu Cho, Seoul (KR); Su Jung Noh, Bucheon-si (KR)

(73) Assignee: KOREA UNIVERSITY, INDUSTRY & ACADEMY COLLABORATION FOUNDATION OF KOREA UNIVERSITY, INDUSTRY & ACADEMY COLLABORATION FOUNDATION (KR)

( * ) Notice: Subject to any disclaimer, the term of this patent is extended or adjusted under 35 U.S.C. 154(b) by 776 days.

(21) Appl. No.: 11/931,703

(22) Filed: Oct. 31, 2007

(65) Prior Publication Data

US 2009/0155617 A1 Jun. 18, 2009

(30) Foreign Application Priority Data

Nov. 1, 2006 (KR) .................. 10-2006-0107410

(51) Int. Cl.
| | |
|---|---|
| C25D 5/10 | (2006.01) |
| C25D 5/18 | (2006.01) |
| C25D 1/04 | (2006.01) |
| B82Y 5/00 | (2011.01) |
| B82Y 25/00 | (2011.01) |
| H01F 1/00 | (2006.01) |

(52) U.S. Cl.
CPC ... *C25D 1/04* (2013.01); *B82Y 5/00* (2013.01); *B82Y 25/00* (2013.01); *C25D 5/10* (2013.01); *C25D 5/18* (2013.01); *H01F 1/0009* (2013.01); *H01F 1/0081* (2013.01); *Y10T 428/1259* (2015.01); *Y10T 428/12465* (2015.01); *Y10T 428/12632* (2015.01)

(58) Field of Classification Search
CPC .............. C25D 5/10; C25D 5/18; C25D 3/20; C25D 3/48
USPC .................................. 205/102, 104
See application file for complete search history.

(56) References Cited

U.S. PATENT DOCUMENTS

| | | | |
|---|---|---|---|
| 3,902,977 A | * | 9/1975 | Greenspan .................. 205/251 |
| 4,652,348 A | | 3/1987 | Yahalom et al. |
| 4,808,279 A | * | 2/1989 | Moskovits et al. .......... 205/105 |

(Continued)

FOREIGN PATENT DOCUMENTS

| | | |
|---|---|---|
| GB | 1433850 | 4/1976 |
| WO | 01/23645 A1 | 4/2001 |
| WO | 01/25510 A1 | 4/2001 |

OTHER PUBLICATIONS

Arthur Rose et al, The Condensed Chemical Dictionary, seventh edition, Reinhold Book Corporation, New York, 1968, pp. 514.*

(Continued)

*Primary Examiner* — Bryan D. Ripa

(57) ABSTRACT

Disclosed are an Fe—Au barcode type nanowire and a method of manufacturing the same. The nanowire has a magnetic-optical multifunction and is suitable for adjusting magnetic intensity thereof. The Fe—Au nanowire has a multilayered structure, in which an iron layer and a gold layer are alternately and repeatedly formed, and is formed in a single plating bath through a pulse electro-deposition.

12 Claims, 9 Drawing Sheets

A: ANODIC ALUMINUM OXIDE NANOTEMPLATE
B: DEPOSITING SILVER ELECTRODE LAYER
C: ELECTRO-DEPOSITING FE/AU BARCODE NANOWIRE
D: REMOVING NANOTEMPLATE (REMOVING TOGETHER WITH ELECTRODE LAYER)

(56) References Cited

U.S. PATENT DOCUMENTS

| | | | |
|---|---|---|---|
| 4,869,971 A * | 9/1989 | Nee et al. | 428/635 |
| 4,904,349 A * | 2/1990 | Tokushima et al. | 205/102 |
| 6,547,944 B2 * | 4/2003 | Schreiber et al. | 205/96 |
| 6,565,732 B1 * | 5/2003 | Kitada et al. | 205/267 |
| 6,902,827 B2 * | 6/2005 | Kelly et al. | 428/635 |
| 7,045,049 B1 * | 5/2006 | Natan et al. | 205/118 |
| 2001/0020590 A1 * | 9/2001 | Duruz et al. | 205/333 |
| 2002/0055239 A1 | 5/2002 | Tuominen et al. | |
| 2005/0171433 A1 | 8/2005 | Boppart et al. | |
| 2007/0221917 A1 * | 9/2007 | Chin et al. | 257/40 |
| 2007/0224399 A1 * | 9/2007 | Rabin et al. | 428/209 |

OTHER PUBLICATIONS

F. A. Lowenheim, Electroplating, McGraw-Hill Book Company, New York, 1978, pp. 16-19.*

Robert W. Weast, Handbook of Chemistry and Physics, CRC Press, Cleveland, Ohio, 1976, pp. D141 to D-147.*

Robert C. O'Handley, Modern Magnetic Materials, John Wiley & Sons, Inc., p. 125, 2000.

L. Sun et al., Turning the Properties of Magnetic Nanowires, IBM J. Res. & Dev., vol. 49, p. 82, 2005.

* cited by examiner

A: ANODIC ALUMINUM OXIDE NANOTEMPLATE

B: DEPOSITING SILVER ELECTRODE LAYER

C: ELECTRO-DEPOSITING FE/AU BARCODE NANOWIRE

D: REMOVING NANOTEMPLATE
(REMOVING TOGETHER WITH ELECTRODE LAYER)

* perp. : perpendicular to wire axis
* para. : parallel to wire axis

IRON-GOLD BARCODE NANOWIRE AND MANUFACTURING METHOD THEREOF

BACKGROUND

The present invention relates to a barcode nanowire and a method of manufacturing the same.

Metal nanopartieles are extensively applied to various fields, such as microelectronics, a light quantum technology, a catalyst reaction, a biotechnology, etc. Recently, various studies have been conducted in fields of a high density magnetoresistance memory and a giant magnetoresistance sensor to provide a method of synthesizing a nanowire using a nanotemplate because a size, a shape and crystallinity of a nanowire structure can be adjusted by using a nanotemplate structure. In addition to these studies, a multi-layer nanowire structure has been suggested not only to utilize inherent property of each layer, but also to create new applications through a synergy effect among the layers having different roles.

Especially, in a biotechnology field, studies based on Au, that is, studies for providing functions to an Au-based structure have been extensively conducted. In particular, since Au represents unique optical and chemical properties, studies have been performed to utilize Au in various medical applications, such as a high sensitivity-diagnostic analysis, an imaging and a medical treatment using the photonics, deliveries of drug and gene, a thermal ablation and a radiotherapy. A functional Au coating may provide a surface where nanoparticles can be provided together with a bio-marker or a bio-linker that is attachable to the Au surface.

Meanwhile, Fe has an advantage in terms of magnetic property. Especially, studies have been widely performed to control a movement of a nanostructure using the magnetic property in various fields including a contrast media of magnetic resonance imaging (MRI), additives to a hyperthermia, a chemotherapy and a radiotherapy for malignant cells, a cell membrane control, a magnetic separation, a cell arrangement, a tracking of paths for a labeled cell and other biological material, a drug delivery, drugs applied to a specific region, a genetic treatment and a nuclear treatment, a nanoprobe and a bio-sensor that are regarded as potential life science applications and potential medicine applications.

The nanowire having the multi-layer structure has various advantages suitable for conditions (Au layer to provide functionality and Fe layer to provide magnetic property) required for the biotechnology in addition to a basic property of the nanowire obtained by synthesizing materials having biocompatibility. The synthesized nanowire is applicable for fields where the property of each material is utilized and may create new markets based on the synergy effect of the materials having various properties.

However, although the studies relating to a multi-layered nanostructure and a barcode nanowire have been extensively performed, a study for a nanowire having the biocompatibility and a magnetic-optical multifunction has not been performed yet. Especially, the size of the nanostructure is an important factor in the biomedical applications, so that the size of the nanostructure must be adjusted corresponding to a cell (10-100 μm), a virus (20-450 nm), a protein (5-50 nm), and a gene (width of 2 nm and length of 10-100 nm). Accordingly, it is necessary to perform a study to provide a barcode type biocompatible nanowire satisfying the above requirements.

SUMMARY

An object of the present invention is to provide a barcode nanowire having a multi-layered structure of Fe—Au and a method of manufacturing the same. The nanowire having the multi-layered structure represents the magnetic-optical multifunction so that it is applicable for a biotechnology.

Another object of the present invention is to provide a hybrid nanowire having a core-shell structure including iron oxide-gold or (iron, iron oxide)-gold and a method of manufacturing the same capable of easily adjusting magnetic intensity and having the biocompatibility.

A barcode nanowire according to the present invention comprises a first layer including having iron and a second layer including having gold, wherein the first and second layers are alternately stacked on each other. Especially, the first and second layers are alternately stacked lengthwise along a longitudinal direction of the barcode nanowire.

In addition, the barcode nanowire according to the present invention has a (Fe—$Fe_xO_y$)—Au structure, in which the first layer includes an iron layer formed at a center portion of the first layer and an iron oxide layer surrounding the iron layer and the second layer includes a gold layer. The first and second layers are alternately stacked lengthwise along a longitudinal direction of the nanowire. The iron oxide layer includes any one selected from the groups consisting of FeO, $Fe_3O_4$, $\gamma$-$Fe_2O_3$ and $\alpha$-$Fe_2O_3$.

Further, the barcode nanowire according to the present invention has the iron oxide layer serving as the first layer including any one selected from the groups consisting of FeO, $Fe_3O_4$, $\gamma$-$Fe_2O_3$ and $\alpha$-$Fe_2O_3$, and the gold layer serving as the second layer. The first and second layers are alternately stacked lengthwise along a longitudinal direction of the nanowire.

A method of manufacturing a barcode nanowire having a superior biocompatibility according to the present invention comprises the steps of preparing a nanotemplate having pores and representing an insulating property, disposing the nanotemplate in an electrolytic solution including a first precursor for generating an iron ion and a second precursor for generating a gold ion, and performing an electro-deposition to alternately and repeatedly form an iron layer and a gold layer in the pore. The step of electro-deposition step includes a first step of forming the iron layer by applying a first current and a second step of forming the gold layer by applying a second current, wherein the second current has a current density lower than the current density of the first current, and the first and second steps are alternately and repeatedly performed until the nanowire has a required length. The second precursor generates a gold (I) cation while dissociating in the electrolytic solution.

In addition, the method of manufacturing the barcode nanowire according to the present invention further comprises the step of completely or partially oxidizing the iron layer of the nanowire to form an iron oxide layer after performing the electro-deposition step. The current density of the first current is 10 mA/$cm^2$ or above and the current density of the second current is 2 mA/$cm^2$ or below.

DETAILED DESCRIPTION OF THE EMBODIMENTS

Hereinafter, a Fe—Au barcode nanowire and a method of manufacturing the same according to the present invention will be described in detail with reference to accompanying drawings.

[First Embodiment]

The present embodiment provides a method of manufacturing a multilayered Fe—Au barcode nanowire including iron and gold that are formed in a single plating bath through a pulsed electro-deposition using a nanotemplate.

Figure 1:
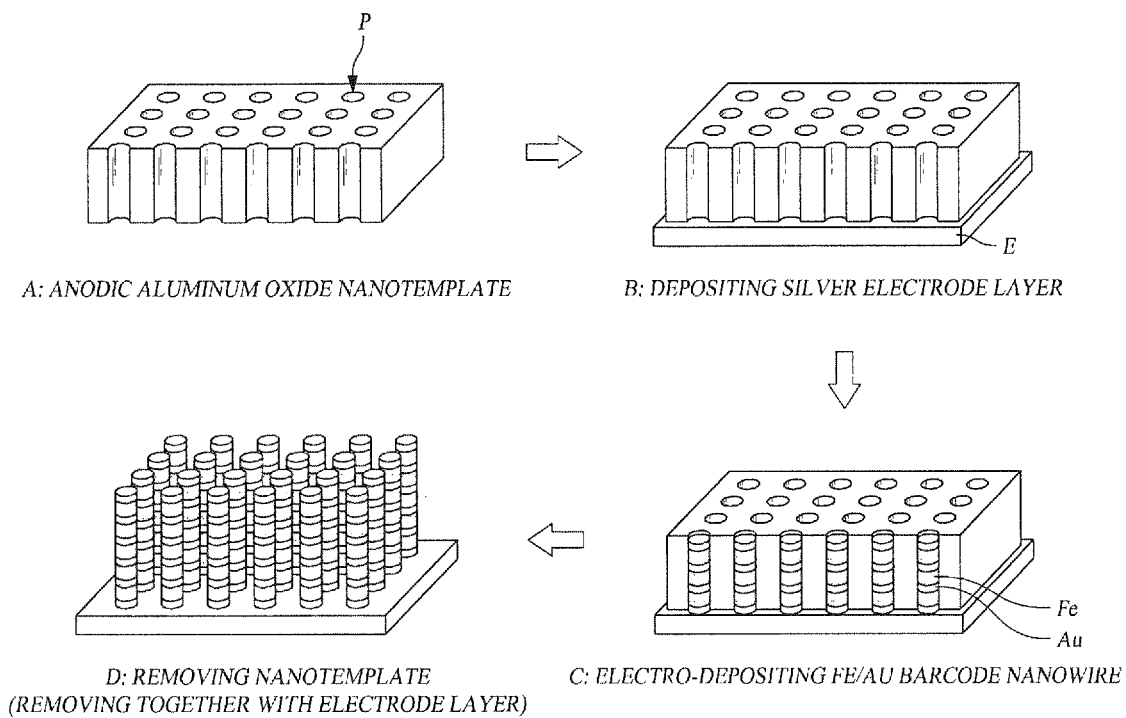
FIG. 1 shows schematic diagrams illustrating processes for manufacturing Fe—Au barcode nanowires according to the present invention.

FIG. 1 shows schematic diagrams illustrating processes for manufacturing Fe—Au barcode nanowires according to the present invention.

FIG. 1A shows a nanotemplate. The nanotemplate includes an anodic aluminum oxide (AAO) nanotemplate, an inorganic nanotemplate or a polymer nanotemplate. Especially, the anodic aluminum oxide nanotemplate is suitable for controlling a shape and a size of nanowire pores. The size of the nanowire is determined based on a diameter of the pores of the nanotemplate, and a length of the nanowire is determined based on a time and a speed of forming the nanowire. The anodic aluminum oxide nanotemplate according to the present embodiment has a pore width of 60 μm and a pore diameter of 200 nm.

After that, as shown in FIG. 1B, an electrode layer (E) is formed on a lower surface of the anodic aluminum oxide nanotemplate through an electron beam evaporation method before performing an electroplating process. The electrode layer includes gold or silver, which has a width of 250 nm and serves as a cathode during an electro-deposition. The electrode layer may include material having a high conductivity other than gold or silver. Although not shown in the drawing, platinum is used as a counter electrode, that is, an anode during the electro-deposition process.

The nanotemplate obtained through the above procedure is disposed in an electrolytic solution for the electroplating process. The electrolytic solution is obtained by mixing a precursor for generating an iron ion and a precursor for generating a gold ion with deionized water at a predetermined molarity ratio. In addition, $H_3BO_3$ serving as a buffer solution may be added to the electrolytic solution, so that an acidity (pH) of the electrolytic solution is constantly maintained at a level of 3.4~3.5, thereby maintaining a homeostasis of a current.

Especially, since two types of precursors must be put in a single plating bath to form a single nanowire layer, the two precursors must be selected from groups that do not create a compound through interaction. That is, each element must be maintained in an ionized state. Since non-cyanide based gold (III) may create a compound through reaction with iron ions (2+, 3+) so that the gold is maintained in a non-ionized state. Thus, cyanide-based gold is preferably used. A precursor that generates a gold (I) cation when it is dissociated in the electrolytic solution is more preferred.

In addition, the mixing ratio of reducible elements and non-reducible elements introduced in the plating bath is controlled, such that elements of the multilayered nanostructure can be separated in the multilayered structure. The morality ratio of Fe ion to Au ion (i.e., Fe:Au) is within a range of 4:1 to 40:1 (preferably, 16:1). That is, the single nanowire layer including two types of elements is formed by relatively lowering molarity of gold, which is a precious metal. According to the present embodiment, the precursor for generating Fe ion includes Iron (II) Sulfate Heptahydrate ($FeSO_4 \cdot 7H_2O$; 278.02 g/mol), and the precursor for generating Au ion includes Potassium dicyanoaurate (I) ($KAu(CN)_2$; 288.10 g/mol).

FIG. 1C shows a multilayered nanowire in which an Fe layer and an Au layer are alternately stacked on pores (P) of the anodic aluminum oxide nanotemplate. In detail, the nanotemplate is disposed in the electrolytic solution described above and a pulse electro-deposition is performed to form a multilayered barcode type nanowire.

In the electro-deposition, the Fe layer is synthesized under high voltage or high current and Au layer is synthesized under low voltage or low current. Accordingly, the Fe layer and the Au layer can be alternately formed in the pores of the nanotemplate by alternately applying voltage and current having different levels while changing current density thereof. According to the present embodiment, the Fe layer is formed by applying a current of about 10 mA/cm² or above and the Au layer is formed by applying a current of about 2.0 mA/cm² or below. Fe and Au have different electrochemical potentials. The Fe layer and Au layer can be formed at a relatively high current and a relative low current, respectively, using the difference of the electrochemical potential, thereby obtaining the Fe/Au nanowire. A diameter of the nanowire is controlled by using an anodic aluminum oxide nanotemplate having different pore sizes, and thicknesses of the Fe layer and the Au layer is controlled by varying the process time for the electroplating.

Meanwhile, two plating baths can be used such that the Fe layer is formed in one plating bath and the Au layer is formed in the other plating bath. However, in the case that two plating baths are used to form the Fe—Au multilayered nanowire, the Au layer is not easily deposited on the Fe layer through the electro-deposition since the oxidation of Fe is rapidly performed. Therefore, according to the present invention, the Fe layer and the Au layer are formed by using a single plating bath to ensure stability of the manufacturing process and improve the product yield.

After that, as shown in FIG. 1D, in order to obtain an individual nanowire, the anodic aluminum oxide nanotemplate is etched in a sodium hydroxide (NaOH) solution at a normal temperature for one hour. The sodium hydroxide solution selectively removes the anodic aluminum oxide nanotemplate without etching the Fe layer, so that a barcode type Fe—Au nanowire is formed.

Figure 2:
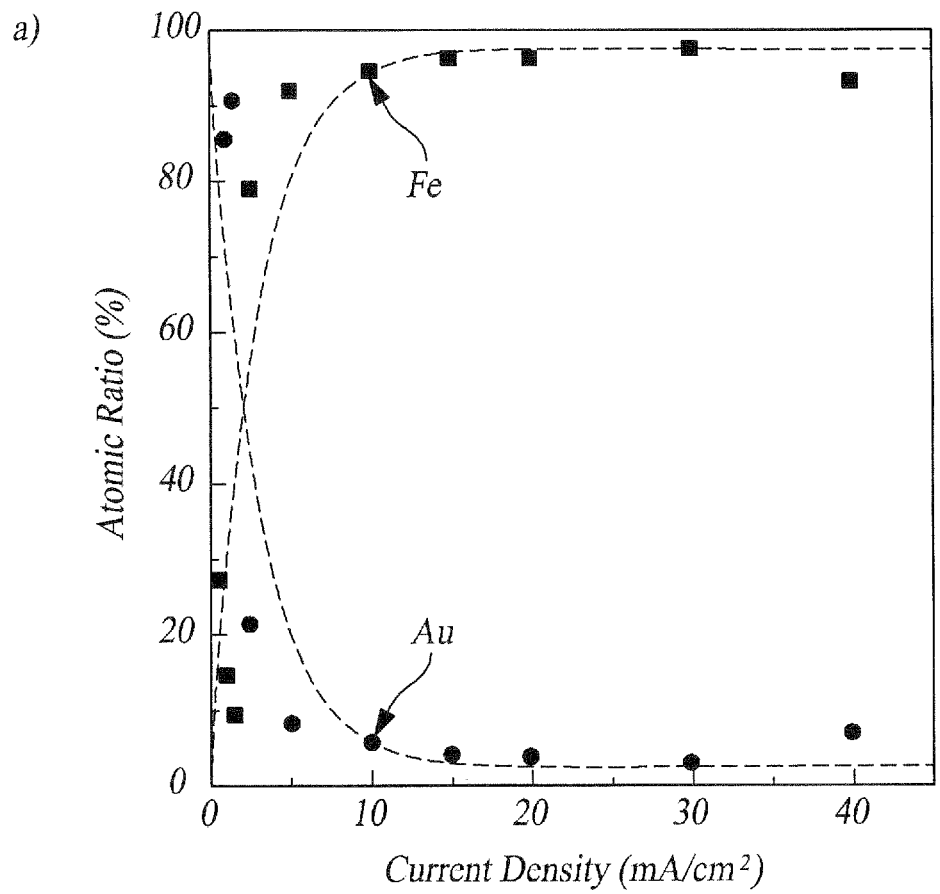
FIG. 2A shows composition-current density profile of the nanowire samples each obtained at a given continuous current density (the signs of square and dots represent Fe and Au, respectively, and the dash lines are for visual guide.)
FIG. 2B shows a FE-SEM image of the Fe—Au barcode nanostructures in AAO.
Figure 2:
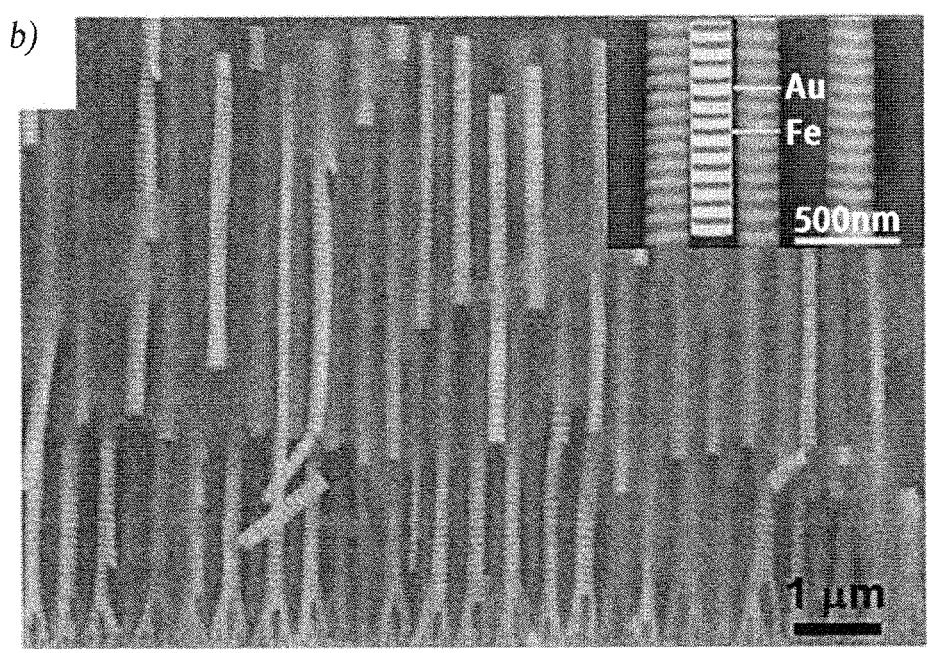

The selection of a current density to electro-deposit Fe or Au is determined based on the evaluation of the composition-current density profile, which is acquired from the analysis of the samples each obtained at a given constant current density, by inductively coupled plasma atomic emission spectrophotometer (ICP-AES) (FIG. 2A). According to the data, the iron or gold composition in the electro-deposited nanowires changes rapidly with the current density, indicating no formation of an alloy between the two elements, as expected from their binary phase diagram. It is apparent that a single-component nanowire can be acquired under a current above 10 mA/cm$^2$ for Fe and below 2 mA/cm$^2$ for Au, preferably, under 30 mA/cm$^2$ for Fe and 1 mA/cm$^2$ for Au. However, If a current density is more than 50 mA/cm$^2$ for Fe, the uniformity of the resultant nanowire can be deteriorated. In addition, if a current density is less than 0.2/cm$^2$ for Au, the electro-deposition speed is too slow and the template can be damaged due to the acidic environment.

Figure 3:
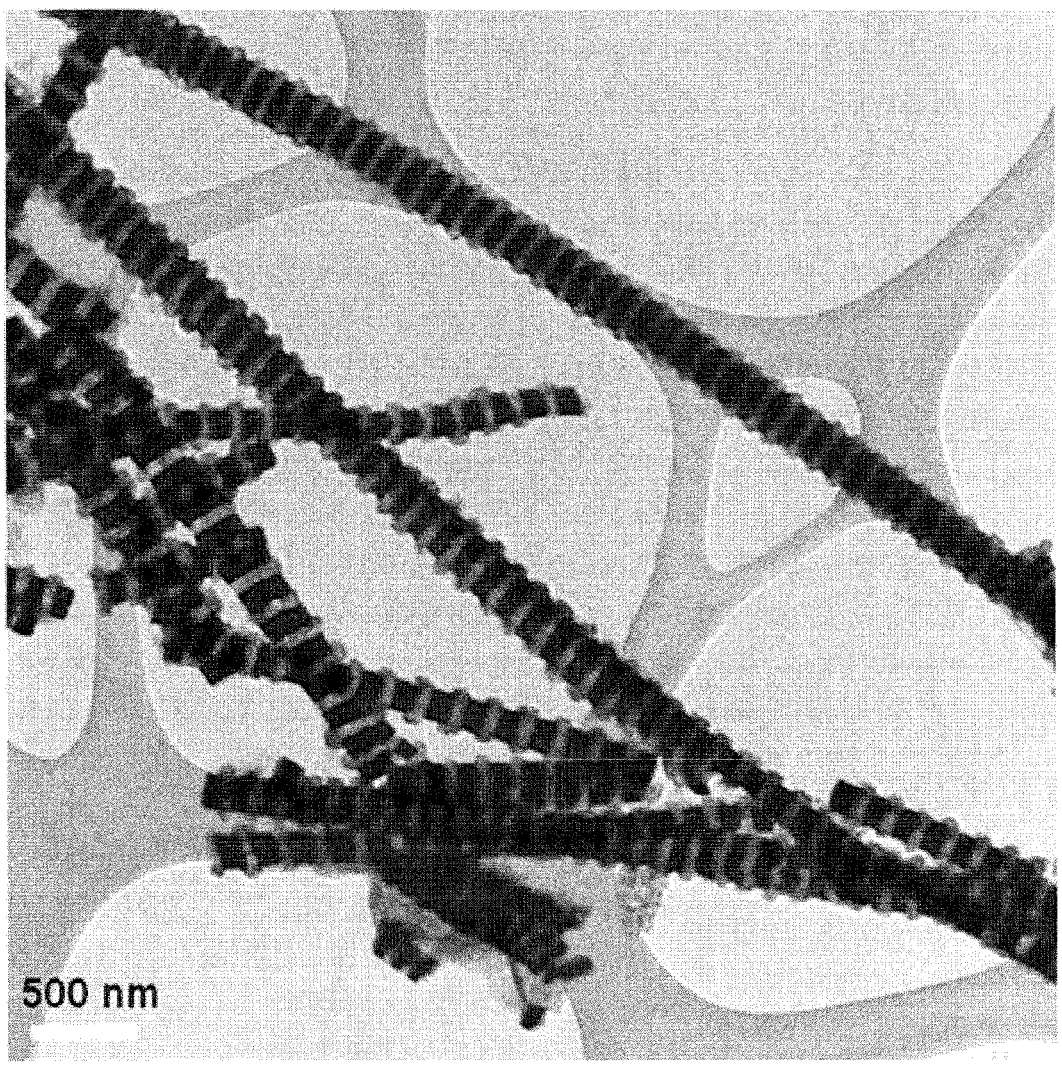
FIG. 3 represents a bright-field TEM image of freestanding Fe—Au barcode nanowires, showing well-separated, alternate white and black parts that correspond to Fe and Au layers.

As shown in FIG. 2B, the inspection by a field-emission scanning electron microscope (FE-SEM) demonstrates the well-formed barcode nanowires embedded in the array of the AAO nanopores (sample prepared under pulse electro-deposition of 10 mA/cm$^2$ for Fe and 0.5 mA/cm$^2$ for Au). The nanowires are, as clearly shown in the inset, composed of two alternative segments, representing the Fe and Au components, respectively. The inset presents the enlarged image of several of the barcode nanowires, with a schematic representing the arrangement of alternative Fe (black parts) and Au (white parts) segments in a single nanowire. The finding is substantiated by transmission electron microscopy (TEM) observation of the nanowires after removal of the nanotemplate, as shown in FIG. 3 (sample prepared under pulse electro-deposition of 10 mA/cm$^2$ for Fe and 0.5 mA/cm$^2$ for Au). In the bright-field low magnification image, the free-standing Fe—Au barcode nanowires show well-separated, bamboo-like nanostructures. The contrast between the black and bright segments is distinct, indicating a clear-cut nanostructure. The composition of the segments was identified by the means of elemental line-scan and mapping as given in FIG. 5.

Figure 4:
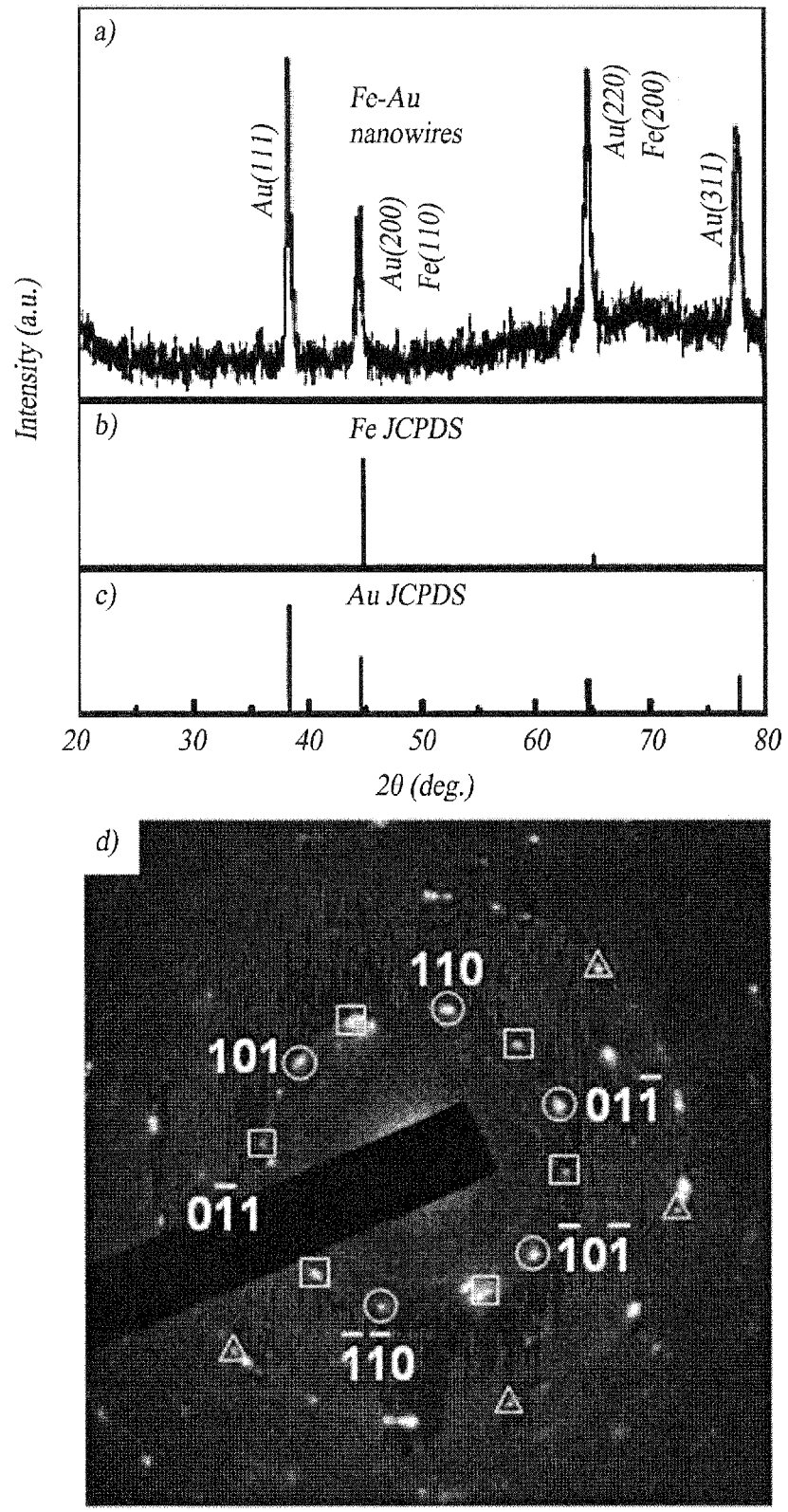
FIG. 4A shows the XRD pattern for the Fe—Au barcode nanowire array in AAO, compared to the standard b) Fe and c) Au JCPDS data.
FIG. 4D shows the SAED pattern taken from one Fe segmental region.

The crystal structure of the Fe—Au barcode nanowires was characterized by x-ray diffraction (XRD), as shown for the sample prepared under pulse electro-deposition of 10 mA/cm$^2$ for Fe and 0.5 mA/cm$^2$ for Au. In FIG. 4, the diffraction of the nanowires is compared to the standard diffraction peaks (in bars) of the corresponding constituent materials (JCPDS nos. 87-0721 and 04-0784). As labeled in the pattern, the peaks at 38.14°, 44.36°, 64.58° and 77.44° may be assigned to Au (111), (200), (220) and (311), while the peaks at 44.36° and 64.58° at the same time belong to Fe (110) and (200).

Figure 5:
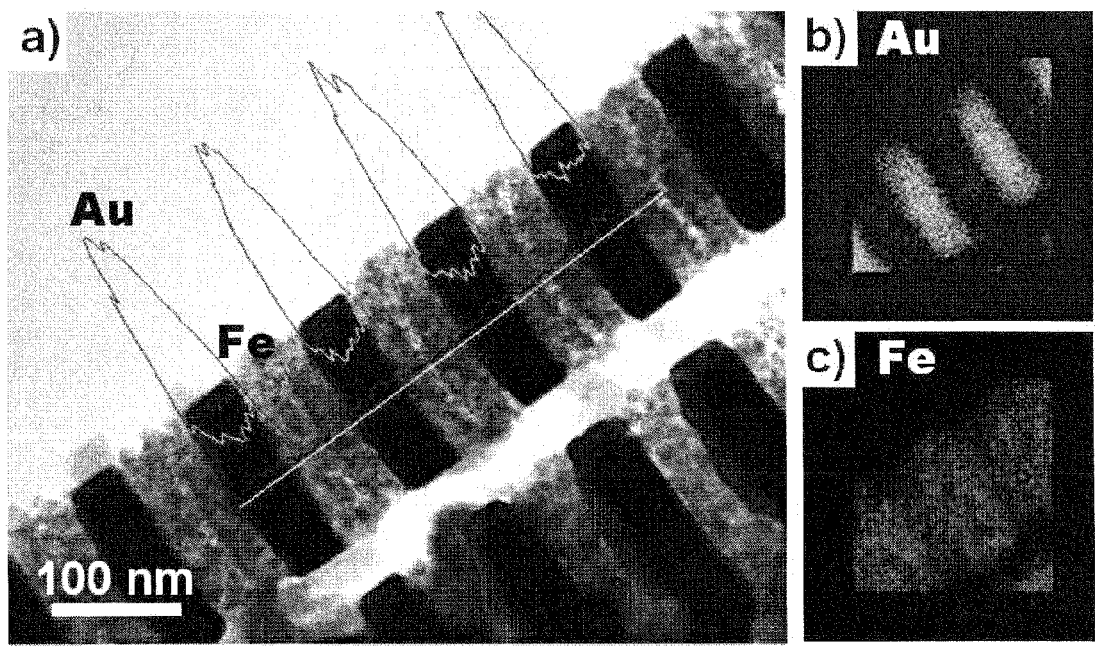
FIG. 5 shows the TEM analysis of a freestanding Fe—Au barcode nanowire: a) TEM elemental line scanning of Fe and Au composition along the nanowire; b) TEM elemental mapping of Au; c) TEM elemental mapping of Fe.

As a result of superimposition between the peaks of Fe (110)/Au (200) and Fe (200)/Au (220), the presence of iron in elemental state is derived from the selected-area electron diffraction (SAED) pattern (FIG. 4D) taken from the Fe segment determined by elemental line-scan and mapping as elucidated in FIG. 5. In the SAED pattern, multiple single-crystal diffraction patterns are recognizable, as labeled by the circles for one set of Fe {110} and the squares for another (The triangles signify the second-order diffraction spots corresponding to the set represented by the circles). The analysis is consistent with the outcome of the SAED pattern obtained from nanowires deposited at a continuous current density of 10 mA/cm$^2$, which proves iron in the elemental state. Moreover, the absence of Au (111) in FIG. 4D supports the assignment of the spots to the elemental iron. Besides, average crystalline domain sizes in the barcode nanowires can be estimated, ~26.1 nm for the Fe segments and ~24.0 nm for the Au segments, from the full width at half maximum (FWHM) in terms of the Scherrer equation.

FIG. 5 shows the TEM micrograph and its corresponding elemental mapping of an individual Fe—Au barcode nanowire after dissolving the AAO nanotemplate (sample prepared under pulse electro-deposition of 30 mA/cm$^2$ for Fe and 0.5 mA/cm$^2$ for Au). From the line scans, it is clear that the nanowire consists of alternative Fe and Au segments, confirming the results observed in FIG. 2B and FIG. 3. The homogeneity of the elemental distribution in the Fe and Au segments is revealed in the elemental mapping in FIG. 5B and FIG. 5C.

Figure 6:
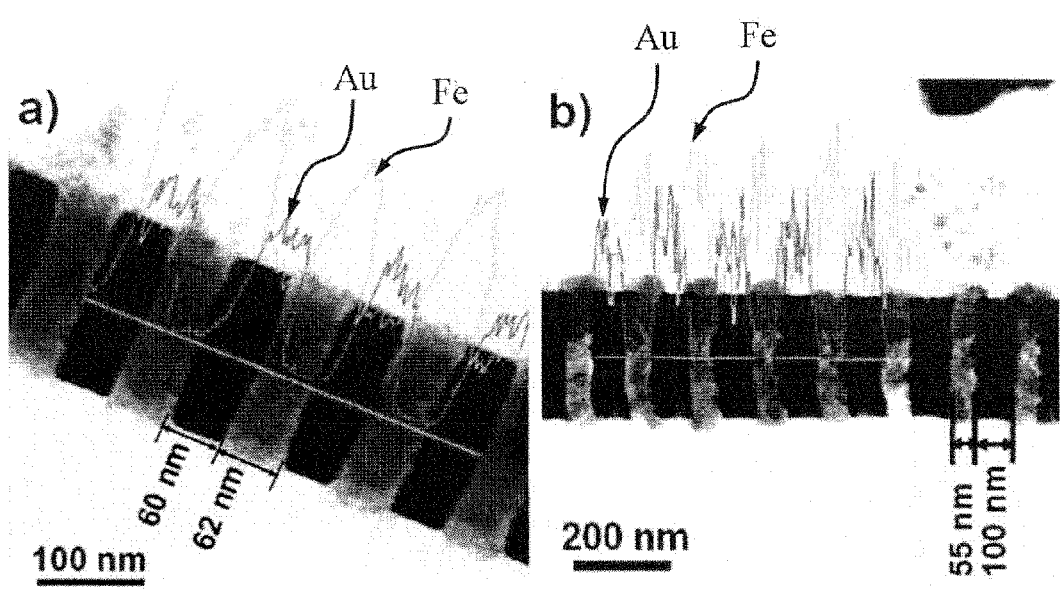
FIG. 6 shows TEM images of free-standing Fe—Au barcode nanowires of different segmental lengths, with TEM elemental line scanning of Fe and Au composition along the nanowires via EDAX: a) Segmental length ratio ~1; b) Segmental length ratio ~0.5.

The tailoring of the barcode nanostructure in the Fe—Au nanowires was achieved by regulating the pulse durations. FIG. 6 presents two examples of various Fe and Au segmental lengths, prepared by different electro-deposition pulses under the current densities of 10 mA/cm$^2$ for Fe and 0.5 mA/cm$^2$ for Au. In one case (FIG. 6A), the Fe and Au segments are 62 nm and 60 nm, or the segmental length ratio is almost one, whereas in the other case (FIG. 6B), the Fe and Au segments are 55 nm and 100 nm, or the segmental length ratio is about 0.5. The change in the barcode nanostructure should be reflected in its properties, as discussed below in the context of magnetism.

The magnetic properties of Fe—Au barcode nanowires of different segmental lengths were compared by means of a vibrating sample magnetometer (VSM) at room temperature. The results of the Fe—Au barcode arrays as shown in FIGS. 6A and 6B were given in FIGS. 7A and 7B. The external magnetic field was applied parallel and perpendicular to the nanowire axis, respectively. It is obvious that both Fe—Au barcode arrays have their easy-axis parallel to the nanowire axis and show soft ferromagnetic properties. In the case of the segmental length ratio ~1, the coercivities are 58 Oe and 28 Oe for parallel and perpendicular to the wires, while in the case of the segmental length ratio ~0.5, the coercivities are 42 Oe and 36 Oe for parallel and perpendicular to the wires.

Figure 7:
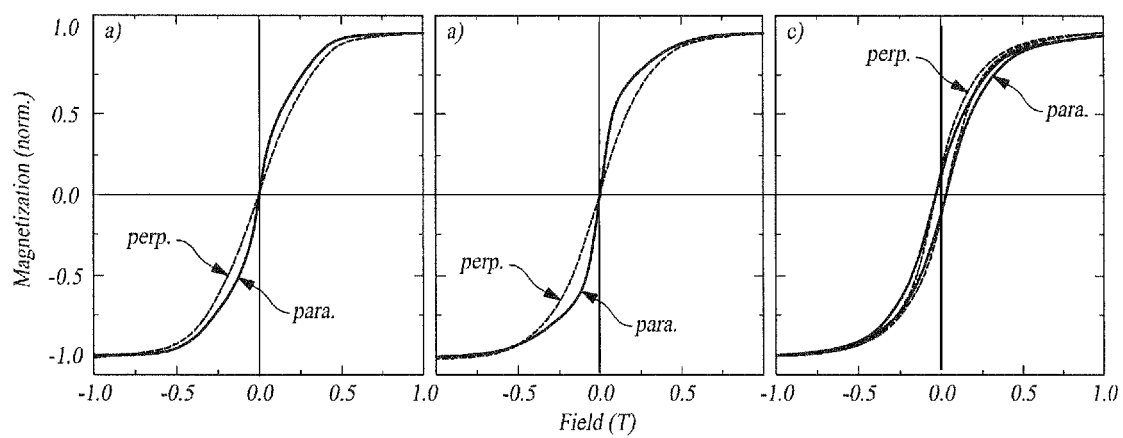
FIG. 7 shows Hysteresis curves measured at room temperature for the Fe—Au barcode nanowire arrays in AAO as given in FIGS. 6A and 6B: a) segmental length ratio ~1; b) segmental length ratio ~0.5; c) pure Fe nanowire array.

The magnetic remanence is almost zero for both cases. In comparison, FIG. 7C gives the measurement obtained for the Fe nanowire array deposited at a continuous current density of 10 mA/cm$^2$. Its hysteresis curves are almost identical in both parallel and perpendicular directions, with the weak easy-axis perpendicular to the nanowires and the coercivities of 300 Oe and 340 Oe, correspondingly. The result is in striking contrast to the commonly observed phenomena that the easy-axis of the Fe nanowire arrays is along the nanowire axis. In fact, the easy-axis of magnetic nanowire arrays is a complex issue that needs to be handled meticulously. Factors such as shape and magnetocrystalline anisotropies, dipole-dipole interactions and surface anisotropy as well in small dimension have dominant influence to determine the direction of the easy-axis. Indeed, the easy-axis switch is detected in our Fe—Au barcode nanosystem when the individual layer thicknesses were ~110 nm for Fe layer and ~30 nm for Au layer.

Figure 8:
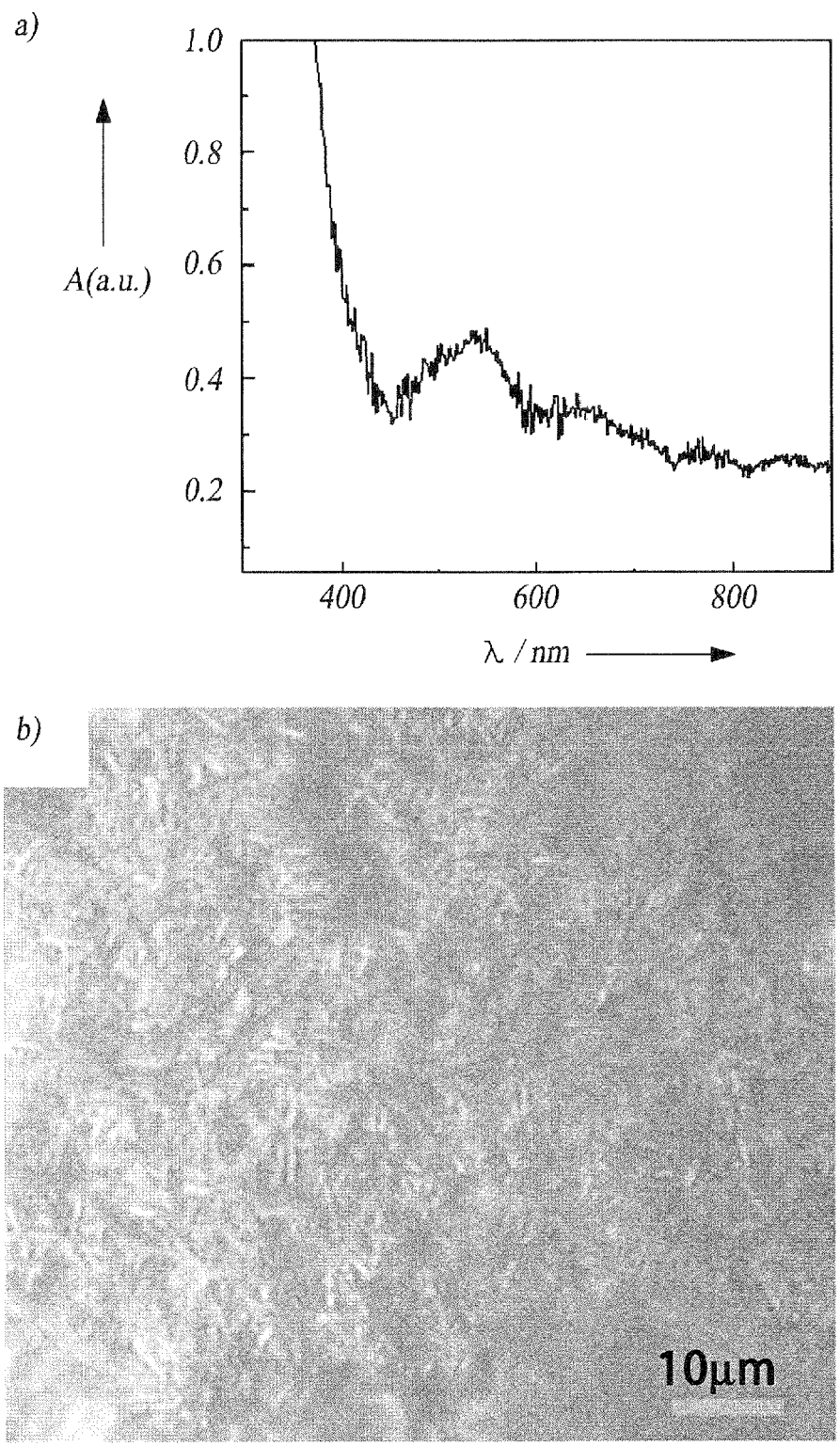
FIG. 8 shows optical measurements of the Fe—Au barcode nanowires: a) UV-Vis absorption spectrum of the Fe—Au barcode nanowires after thiolation in ethanol; b) Bright-field reflectance image.

It is well-known that nanostructured Au (e.g., nanoparticles and nanowires) exhibit an absorption band in the visible region owing to the surface plasmon (SP), which is characteristic of the dimension, shape and physicochemical environment surrounding the Au nanostructure. FIG. 7A shows the UV-Vis absorption spectrum of the Fe—Au barcode nanowires after thiolation to improve dispersion, prepared under pulse electro-deposition of 10 mA/cm² for Fe and 0.5 mA/cm² for Au. The plasmon arising in the barcode nanowires are characteristic of the unique optical property of gold nanostructure. The absorption feature peaking at ~530 nm and ~660 nm reflects the outcome of the shaped Au segments. The shifting and band shape is expected to depend on the Au segmental lengths. Although the direct contribution of the Fe segments to the spectrum is negligible, the close proximity of the nanomagnetic Fe to the Au segments may exert influence on the optical properties of the nanowires. We notice that the weak absorption located at ~770 nm and ~850 nm could be due to the coupling between the Au segments. FIG. 8B is an image acquired using a Nikon Optiphot-100.

[Second Embodiment]

The present invention provides a method of manufacturing a hybrid (iron, iron oxide)-gold nanowire by oxidizing the Fe—Au nanowire obtained through the first embodiment.

Figure 9:
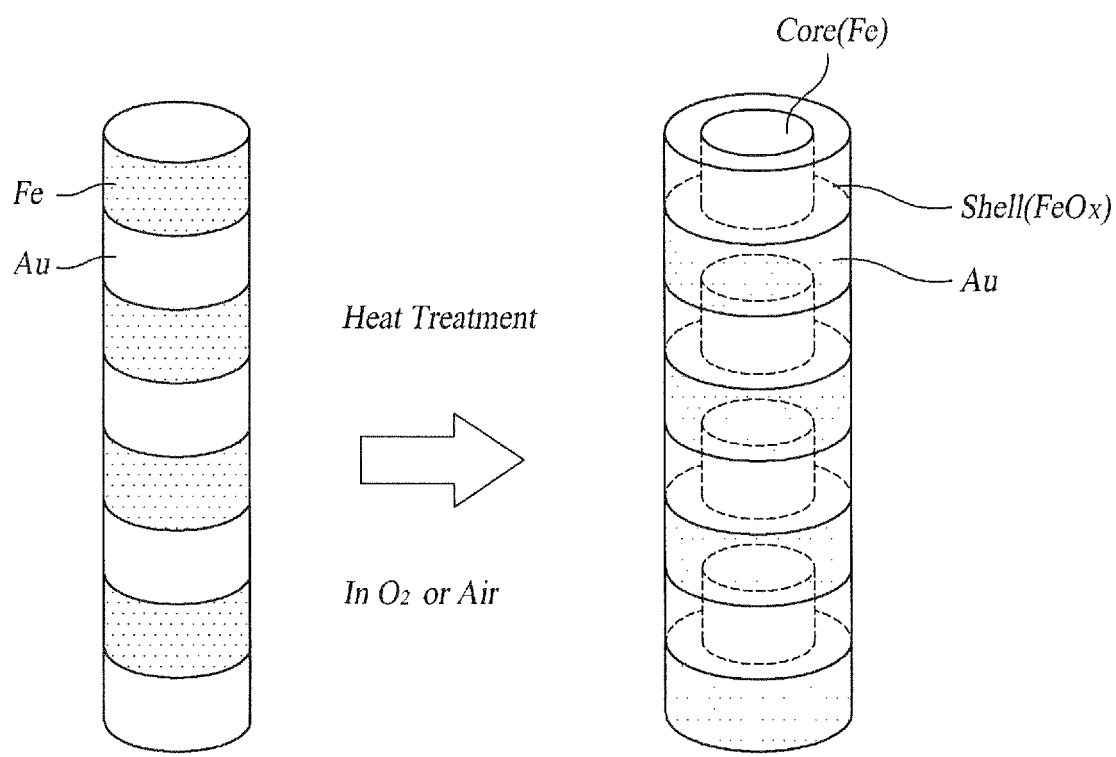
FIG. 9 is a schematic illustration showing formation of a (Fe, $Fe_xO_y$)—Au hybrid nanowire from a Fe—Au barcode nanowire.

In detail, the Fe—Au nanowire obtained through the first embodiment is heat-treated in an oxygen atmosphere (for example, $O_2$ or Air). The relatively stable gold layer does not form an oxidized layer. However, the Fe layer is easily oxidized, so that an iron oxide layer is formed on a surface of the Fe layer toward the center thereof. Accordingly, the entire Fe layer is changed into the iron oxide layer or partially oxidized. Thus, the center portion of the Fe layer remains as the iron layer and a surface of the Fe layer remains as the iron oxide layer. The structure having partially oxidized iron layer is referred to as a hybrid structure. FIG. 9 schematically represents the formation of an (Fe, $Fe_xO_y$)—Au hybrid nanowire. Meanwhile, the oxidizing of iron is performed after performing the electro-deposition process or after removing the nanotemplate.

The temperature and the time for the heat-treatment serve as critical process-variables during the heat-treatment in the oxygen atmosphere. Various iron oxides may be formed on a surface of the nanowire corresponding to the temperature. Various types of iron oxides can be provided by controlling the heat-treating temperature. In addition, the iron oxides having at least two phases can be obtained and the phase can be controlled by adjusting the heat-treating temperature. Since the oxidation occurs from the surface of the iron, the hybrid type nanowire including a core-shell structured iron layer can be synthesized within a short period of time through the heat-treatment process. If the heat-treatment is performed for a long time, the iron layer is completely oxidized, so that the barcode type nanowire structure having $Fe_xO_y$—Au structure is realized. As a reference, Table 1 represents data in which the phase, magnetism type, and crystal structure of iron oxides are provided for comparison (Robert C. O'Handley, "Modern Magnetic Materials", John Wiley & Sons, Inc., p.p. 125, 2000, L. Sun et al, "Turning the properties of magnetic nanowires", IBM J. Res. & Dev., vol. 49, p.p. 82, 2005).

TABLE 1

| Phase | Magnetism Type | $M_s$ (emu/g) | Crystal Structure |
| --- | --- | --- | --- |
| Iron (Fe) | Ferromagnetic | 218 | Body Centered Cubic |
| Wüstite (FeO) | Antiferromagnetic | 0 | Rocksalt |
| Maghemite ($\gamma$-$Fe_2O_3$) | Ferromagnetic | 74 | Metastable defective spinel |
| Magnetite ($Fe_3O_4$) | Ferromagnetic | 84 | Spinel |
| Hematite ($\alpha$-$Fe_2O_3$) | Antiferromagnetic | 0 | Corundum |

Meanwhile, as shown in Table 1, the barcode wire having a pure iron layer has a saturation magnetization (M) greater than that of the iron-oxides by three times. Accordingly, the saturation magnetization of the entire nanowire is controlled by controlling the thickness and the type of the iron oxides. In addition, the magnetic core of the nanowire can be surrounded by a non-magnetic shell.

According to the present invention, a Fe—Au barcode type nanowire having the biocompatibility and the magnetic-optical multifunction is formed through a pulse electro-deposition process using a single plating bath. In addition, according to the present invention, the manufacturing process is simplified and the manufacturing cost is reduced. Further, the reproducibility is improved and the shape and the size of the nanowire are easily controlled.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A method of manufacturing a barcode nanowire having a superior biocompatibility, the method comprising the steps of:

preparing a nanotemplate having a pore and representing insulating property;

disposing the nanotemplate in an electrolytic solution including a first precursor for generating an iron ion and a second precursor for generating a gold ion; and performing an electro-deposition to alternately and repeatedly form an iron layer and a gold layer in the pore, wherein the electro-deposition step galvanostaticaly controls how iron ions and gold ions deposit into the pore, the electro-deposition step including a first step of forming the iron layer by applying a first current and a second step of forming the gold layer by applying a second current, the second has a current density lower than a current density of the first current, and the first and second steps are alternately and repeatedly performed until the nanowire has a required length, wherein the density of the first current is in a range of from 10 mA/cm² to 50 mA/cm², and the density of the second current is in a range of from 0.2 mA/cm² to 2 mA/cm², and wherein a molarity ratio of an iron to a gold ion is within a range of 4:1 to 40:1 in the electrolytic solution.

2. The method as claimed in claim 1, further comprising the step of completely or partially oxidizing the iron layer of the nanowire to form an iron oxide layer by heating the nanowire in an oxygen atmosphere at a temperature and time combination selected to form a selected iron oxide.

3. The method as claimed in claim 1, wherein the second precursor generates a gold (I) cation while dissociating in the electrolytic solution.

4. The method as claimed in claim 2, wherein the second precursor generates a gold (I) cation while dissociating in the electrolytic solution.

5. The method as claimed in claim 1, wherein the electrolytic solution includes iron (II) sulfate heptahydrate serving as the first precursor and potassium dicyanoaurate (I) serving as the second precursor.

6. The method as claimed in claim 2, wherein the electrolytic solution includes iron (II) sulfate heptahydrate serving as the first precursor and potassium dicyanoaurate (I) serving as the second precursor.

7. The method as claimed in claim 2, wherein the iron oxide layer includes at least any one selected from the group consisting of FeO, $Fe_3O_4$, $\gamma$-$Fe_2O_3$ and $\alpha$-$Fe_2O_3$.

8. The method as claimed in claim 1, further comprising adding an inorganic acid buffer solution in an electrolytic solution in the electro-deposition step.

9. The method as claimed in claim 8, wherein the inorganic buffer solution comprises $H_3BO_3$.

10. The method as claimed in claim 1, further comprising constantly maintaining an acidity (pH) of an electrolytic solution in the electro-deposition step at a level of 3.4 ~3.5, thereby maintaining a homeostasis of a current.

11. The method of claim 2, wherein the heating time is selected to cause the iron-oxide layer to form a shell over a core of iron in the nanowire that is not oxidized.

12. The method of claim 2, wherein the heating time is selected to cause the iron-oxide layer to completely oxidize the iron in the nanowire to create a $Fe_xO_y$—Au structure for the nanowire.

* * * * *